United States Patent [19]
Moens

[11] Patent Number: 5,907,058
[45] Date of Patent: May 25, 1999

[54] SYNTHESIS OF AN ACID ADDITION SALT OF DELTA-AMINOLEVULINIC ACID FROM 5-BROMO LEVULINIC ACID ESTERS

[75] Inventor: Luc Moens, Lakewood, Colo.

[73] Assignee: Midwest Research Institute, Kansas City, Mo.

[21] Appl. No.: 09/124,489

[22] Filed: Jul. 29, 1998

[51] Int. Cl.$^6$ .................................................. C07C 229/08
[52] U.S. Cl. ............................................................ 562/567
[58] Field of Search ............................................. 562/567

[56] References Cited

U.S. PATENT DOCUMENTS

| | | | |
|---|---|---|---|
| 3,846,490 | 11/1974 | Aronova et al. | 260/534 R |
| 4,325,667 | 4/1982 | Metcalf et al. | 260/349 |
| 5,284,973 | 2/1994 | Ebata et al. | 562/567 |
| 5,344,974 | 9/1994 | Descotes et al. | 562/567 |
| 5,380,935 | 1/1995 | Takeya et al. | 562/567 |

OTHER PUBLICATIONS

Pfaltz and Anwar, Synthesis of . . . Acyl Cyanides, Tetrahedron Letters, vol. 25 (28), pp. 2977–2980, Jun. 1984.

Benedikt and Kost, Synthesis of 5–Aminolevulinic Acid, Zeits. Fur. Natur., 41b (12), pp. 1593–1594, Dec. 1986.

Kawakami et al., A New Synthesis . . 5–Aminolevulinic Acid, Agric. Biol. Chem., 55(6), pp. 1687–1688, Jun. 1991.

Ha et al., Selective . . . 5–Aminolevulinic Acid, Synthetic Communications, 24(18), pp. 2557–2562, 1994.

Neuberger and Scott, The Synthesis . . . Related Compounds, J. of the Chem. Soc., pp. 1820–1825, Jun. 1954.

Awruch et al., Concerning . . 5–aminodehydrolevulinic . . . , Tetrahedron Letters, No. 46, pp. 4121–4124, Nov. 1976.

Evans and Sidebottom, A Simple . . . delta.–Aminolevulinic Acid, J.C.S. Chem. Comm., pp. 753–754, Sep. 1978.

Herdeis and Dimmerling, A Three–Step . . . delta.–Aminolevulinic Acid, Arch Pharm. 317(4), pp. 304–306, Apr. 1984.

*Primary Examiner*—Gary Geist
*Assistant Examiner*—Rosalynd Keys
*Attorney, Agent, or Firm*—Ken Richardson

[57] ABSTRACT

A process of preparing an acid addition salt of delta-aminolevulinic acid comprising:

dissolving a lower alkyl 5-bromolevulinate and an alkali metal diformylamide in an organic solvent selected from the group consisting of acetonitrile, methanol, tetrahydrofuran, 2-methyltetrahydrofuran and methylformate or mixtures thereof to form a suspension of an alkyl 5-(N,N-diformylamino) levulinate ester; and hydrolyzing said alkyl 5-(N,N-diformylamino) levulinate with an inorganic acid to form an acid addition salt of delta-amino levulinic acid.

10 Claims, No Drawings

SYNTHESIS OF AN ACID ADDITION SALT OF DELTA-AMINOLEVULINIC ACID FROM 5-BROMO LEVULINIC ACID ESTERS

The United States Government has rights in this invention under Contract No. DE-AC36-83CH10093 between the United States Department of Energy and the National Renewable Energy Laboratory, a division of the Midwest Research Institute.

BACKGROUND OF THE INVENTION

1. Field of the Invention

The invention is directed to a new process for synthesizing delta-amino levulinic acid (also known as 5-aminolevulinic acid) as its hydrochloride salt (DALA. HCl), starting from levulinic acid. In particular, the invention method uses sodium diformylamide as a highly reactive and readily accessible reagent for the amination of the C-5 position of methyl 5-bromolevulinate. This process generates an N,N-diformylamido derivative of the levulinate ester that is hydrolyzed with aqueous hydrochloric acid to generate DALA. HCl as a crystalline solid.

2. Description of the Prior Art

Delta-aminolevulinic acid in the salt form (DALA. HCl) is known to have potent herbicidal activity against a broad spectrum of weeds and plants, and is also the subject of studies for use as an antitumor compound in humans. The known synthesis of DALA. HCl that are based on levulinic acid as a starting material are difficult to carry out because of the use of undesirable reagents that are either very toxic or that are not atom economical. In addition, in the currently known synthesis of DALA. HCl, a hazardous chemical step is required to "deprotect" the resulting amino group.

U.S. Pat. No. 5,380,935 discloses a process for preparing 5-aminolevulinic acid or a salt thereof, which comprises reacting furfurylamine, of which the amino group has been protected, with an oxygen molecule under irradiation by light in the presence of a sensitizer, hydrogenating the resulting compound in the presence of a metallic catalyst, and hydrolyzing the hydrogenated compound.

A process for preparation of N-acyl-derivatives of 5-amino levulinic acid as well as the hydrochloride of the free acid is disclosed in U.S. Pat. No. 5,344,974. The process condenses 5-hydroxymethyl furfural with a nitrile in acid solution and the N-acyl aminomethyl furfural compound obtained is converted by photooxidation into a N-acyl-5-aminomethyl-5-hydroxydihydro-2,5-furan-2-one and the latter is reduced with zinc in acetic acid under ultrasonic treatment to N-acyl-5-aminolevulinic acid and by acid hydrolysis the 5-aminolevulinic hydrochloride is obtained.

U.S. Pat. No. 5,284,973 disclose a method of making an acid addition salt of delta-aminolevulinic acid by reacting tetrahydrofurfurylamine with phthalic anhydride under an anhydrous condition to introduce a phthalic group which protects the amino group of tetrahydrofurfuryl amine to give N-tetrahydrofurfuryl pthalimide, carbon atoms of the first- and fourth-positions of the obtained N-tetrahydrofurfurylpthalimide are oxidized at 80° C. using sodium periodate as an oxidizing agent and ruthenium chloride hydrate as a catalyst to yield 5-phthalimidolevulinic acid, and the protecting group of the 5-phthalimidolevulic acid is deprotected using an acid to prepare an acid addition salt of delta-aminolevulinic acid.

A method of producing delta-aminolevulinic acid hydrochloride is disclosed in U.S. Pat. No. 3,846,490. The method comprises acylating hippuric acid with monosuccinate acylchloride in the medium of 65-picoline, subjecting the thus-obtained c-acyl derivative to hydrolysis and isolating the final product.

U.S. Pat. No. 4,325,877 discloses a method of producing delta-aminolevulinic acid by the use of intermediates of bromoketoesters. However, this patent makes use of metal azides in the amination step to convert the bromoketoesters into delta-aminolevulinic acid.

The foregoing prior art methods do not make use of levulinic acid as a starting material for the synthesis of delta-aminolevulinic acid. The starting materials in these methods are acrylic acid ester, 5-hydroxymethyl-furfural, tetrahdyro-furfurylamine, furfurylamine, and hippuric acid.

There is a need in the art of preparing delta-amino levulinic acid to avoid the difficulty of carrying out the process by relying on the use of undesirable reagents that are either very toxic or not atom economical. There is a further need when preparing delta-aminolevulinic acid to avoid the hazardous chemical step normally required to "deprotect" the resulting amino group.

SUMMARY OF THE INVENTION

One object of the present invention is to provide a process for synthesizing delta-aminolevulinic acid as its hydrochloride salt starting from levulinic acid, without the need of using undesirable toxic reagents for the amination step.

Another object of the present invention is to provide a process for synthesizing delta-aminolevulinic acid as its hydrochloride salt starting from levulinic acid, without the need of using undesirable reagents that are not atom economical.

A further object of the present invention is to provide a process for synthesizing delta-aminolevulinic acid as its hydrochloride salt starting from levulinic acid, without the need of using a hazardous chemical step normally required to "deprotect" the resulting amino group.

A still further object of the present invention is to provide a process for synthesizing delta-aminolevulinic acid as its hydrochloride salt starting from levulinic acid, by avoiding the challenging purification steps normally required to isolate DALA. HCl as a crystalline solid.

In general, the invention process is accomplished by the use of sodium diformylamide as a highly reactive and readily accessible reagent for the amination of the C-5 position of methyl-5-bromolevulinate. The reaction of sodium diformylamide with methyl 5-bromolevulinate generates an N,N-diformylamino deriviative of the levulinate ester, namely methyl 5-(N,N diformylamino) levulinate, that is easily hydrolyzed with aqueous hydrochloric acid to generate delta-aminolevulinic acid (also called 5-aminolevulinic acid) as its hydrochloride salt (DALA. Hcl).

DETAILED DESCRIPTION OF THE INVENTION

The invention synthesizes delta-aminolevulinic acid (also called 5-aminolevulic acid) as its hydrochloride salt (DALA. HCl), starting from levulinic acid, which is a product that can be produced from cellulosic materials such as waste paper.

DALA. HCl is known to have potent herbicidal activity against a broad spectrum of weeds and plants, and is also the subject of studies as an anti-tumor compound in humans.

In currently known syntheses of delta-amino levulinic acid in its hydrochloride salt form using levulinic acid as a starting material, it is difficult to carry out the synthesis because of the use of undesirable reagents for the amination step that are either very toxic or that are not atom economical.

The difficulty in current syntheses is further compounded by the need to employ a hazardous chemical step in order to "deprotect" the resulting amino group. For example, in current processes using potassium phthalimide in the amination step for making delta-amino levulinic acid in its hydrochloride salt form, hydrazine is commonly used to "deprotect" the resulting amino group and this results in the disposal of waste that contains phthalic acid, which contains 8 carbon atoms—thereby making the amination step not atom economical, and formidable purification steps are required to isolate DALA. HCl as a crystalline solid.

The synthetic pathway of the invention synthesis of delta-aminolevulinic acid hydrochloride (DALA.HCl) is as follows:

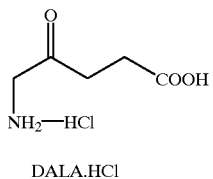

DALA.HCl

EXAMPLE 1

Methyl 5-bromolevulinate (103 mg, 0.49 mmoles) (1) was dissolved in anhydrous acetonitrile (5 mL) under an argon atmosphere and sodium diformylamide (56 mg, 0.59 mmoles) was added in one portion. The resulting suspension was stirred at room temperature for 3 hours, and then heated at reflux temperature for 30 minutes.

The suspension was then filtered through a pad of Celite® and the filtrate was concentrated on the rotary evaporator (at ca. 40° C.). This afforded 101 mg of methyl-5-(N,N-diformylamino) levulinate (2) as a yellowish oil. $^1$ H-NMR 300 MHz (CDCl$_3$, TMS) δ ppm 8.94 (s, 2H, CHO), 4.52 (s, 2H, N—CH$_2$—CO), 3.67 (s, 3H, CH$_3$), 2.81 (t, 2H, J=6.6 Hz, CH$_2$), 2.65 (t, 2H, J=6.6 Hz, CH$_2$). $^{13}$C-NMR 75 MHz (CDCl$_3$, TMS) δ ppm 199.4, 172.3, 163.2, 51.7, 46.8, 34.4, 27.3.

A solution of 101 mg of methyl 5-(N,N-diformylamine) levulinate in 10 ml of 6N HCl was heated at reflux temperature during 30 minutes. Ths solution was then concentrated in vacuo to provide 90 mg of crude delta-aminolevulinic acid hydrochloride (DALA. HCL) as a crystalline solid. $^1$H-NMR showed that this material was identical to commercially available DALA. HCL (purchased from ALDRICH Chem. Co.)

EXAMPLE 2

Same as EXAMPLE 1, except that the methyl 5-bromolevulinate was dissolved in methanol, to produce comparable results.

EXAMPLE 3

Same as EXAMPLE 1, except that the methyl 5-bromolevulinate was dissolved in tetrahydrofuran to produce comparable results.

EXAMPLE 4

Same as EXAMPLE 1 except that the methyl 5-bromolevulinate was dissolved in 2-methyltetrohydrafuran and methylformate to produce comparable results.

The process of the invention is commercially significant because of the avoidance of undesirable reagents for the amination step that are either very toxic or that are not atom economical for current or known synthesis for DALA. HLC, based on the use of levulinic acid as a starting material.

The invention process of using sodium diformylamide as an aminating agent is much easier to use than previously known aminating agents. Therefore, unlike previously known synthetic processes, the method of the invention allows scale-up to industrial scale, using levulinic acid as a feed stock as it avoids the use of undesirable aminating reagents that are very toxic, and only two carbon atoms are removed during the hydrolysis step (i.e. formyl groups), and no challenging purification steps are required to produce DALA. HCl, and this is in strong contrast with the conventional use of potassium phthalimide which resulted in the disposal of waste that contains phthalic acid (eight carbon atoms).

A "lower alkyl" 5-bromolevulinate, in the context of the invention, will mean a carbon length of 1–5, although one carbon or methyl is preferred.

In the preferred embodiment of the invention, sodium diformyl amide is the preferred reagent for amination of the methyl 5-bromolevulinate. However, any alkali metal from group I of the Periodic Table, such as lithium, potassium, cesium or rubidium will work equally well.

Acetonitrile is the preferred organic solvent for dissolution and facilitation of the reaction between methyl 5-bromolevulinate and sodium diformylamide. However, in the context of the invention, other organic solvents such as methanol, tetrahydrofuran, and 2-methyltetrahydrofuran/methylformate and mixtures thereof will work equally well.

The inert atmosphere in which the reaction proceeds is preferrably that of Ar gas; however, any of the inert gases will suffice in the context of the invention process.

Additional advantages and modifications to the invention will be apparent to those skilled in the art. Accordingly, the invention in its broader aspects is not limited to the specific details shown and described. Therefore, various modifications and adaptations may be made without departing from the spirit or scope of the inventive concept as defined by the apended claims and their equivalents.

I claim:

1. A process of preparing an acid addition salt of delta-aminolevulinic acid comprising:

a) dissolving a lower alkyl 5-bromolevulinate and an alkali metal diformylamide in an organic solvent selected from the group consisting of acetonitrile, methanol, tetrahydrofuran, 2-methyltetrahydrofuran and methylformate or mixtures thereof to form a suspension of an alkyl 5-(N,N-diformylamine) levulinate ester; and b) hydrolyzing said alkyl 5-(N,N-diformylamine) levulinate with an inorganic acid to form an acid addition salt of delta-amino levulinic acid.

2. The process of claim 1 wherein said organic solvent is acetonitrile in anhydrous form.

3. The process of claim 2 wherein step a) is carried out in an inert gas atmosphere.

4. The process of claim 3 wherein said inert gas is argon.

5. The process of claim 4 wherein said lower alkyl 5-bromolevulinate is methyl 5-bromolevulinate and said alkyl 5-(N,N-diformylamino) levulinate ester is methyl 5-(N,N-diformylamino) levulinate.

6. The process of claim 5 wherein said inorganic acid is HCl and said acid addition salt of delta-aminolevulinic acid is delta-aminolevulinic acid hydrochloride.

7. The process of claim 6 wherein said alkali metal diformylamide is selected from the group consisting of sodium diformylamide, potassium diformylamide, lithium diformylamide, cesium diformylamide, rubidium diformylamide and mixtures thereof.

8. The process of claim 7 wherein said alkali metal diformylamide is sodium diformylamide.

9. The process of claim 1 wherein said lower alkyl component of 5-bromolevulinate is selected from at least 1 to 5 carbon atoms.

10. The process of claim 1 wherein said lower alkyl component of 5-bromolevulinate is selected from one carbon atom.

* * * * *